(12) United States Patent
Xu et al.

(10) Patent No.: US 11,803,392 B2
(45) Date of Patent: Oct. 31, 2023

(54) ACCIDENTAL-SHUTDOWN-PROOF SWITCH CONTROL APPARATUS AND METHOD FOR ROBOT-ASSISTED SURGICAL DEVICE

(71) Applicant: BEIJING SURGERII ROBOTICS COMPANY LIMITED, Beijing (CN)

(72) Inventors: Kai Xu, Beijing (CN); Aolin Tang, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 275 days.

(21) Appl. No.: 17/418,211

(22) PCT Filed: Dec. 27, 2019

(86) PCT No.: PCT/CN2019/129036
§ 371 (c)(1),
(2) Date: Jun. 24, 2021

(87) PCT Pub. No.: WO2020/135679
PCT Pub. Date: Jul. 2, 2020

(65) Prior Publication Data
US 2022/0083344 A1     Mar. 17, 2022

(30) Foreign Application Priority Data
Dec. 27, 2018   (CN) .......................... 201811610870.5

(51) Int. Cl.
*G06F 9/4401* (2018.01)
*G06F 1/26* (2006.01)
*H03K 17/28* (2006.01)

(52) U.S. Cl.
CPC .............. *G06F 9/442* (2013.01); *G06F 1/263* (2013.01); *H03K 17/28* (2013.01); *H03K 2217/96058* (2013.01)

(58) Field of Classification Search
CPC ..................................... G06F 1/26; G06F 9/44
See application file for complete search history.

(56) References Cited

U.S. PATENT DOCUMENTS

| 6,438,684 B1 * | 8/2002 | Mitchell ................. G06F 9/442 714/24 |
| 6,514,197 B1 | 2/2003 | Ouchi et al. |

(Continued)

FOREIGN PATENT DOCUMENTS

| CN | 1648806 A | 8/2005 |
| CN | 101256518 A | 9/2008 |

(Continued)

OTHER PUBLICATIONS

Office Action in related Korean Application No. 10-2021-7023734 dated Dec. 1, 2022 (14 pages with translation).

(Continued)

*Primary Examiner* — Phil K Nguyen
(74) *Attorney, Agent, or Firm* — Bayes PLLC

(57) ABSTRACT

Apparatuses and methods for preventing accidental-shutdown in a robot-assisted surgical device are disclosed. An exemplary control apparatus includes an on/off key configured to trigger a start action or a shutdown action, an on/off control module configured to detect the shutdown action of the on/off key and obtain a shutdown intention through man-machine interaction, and an on/off hardware circuit configured to detect the start action and send a signal to a power supply. The on/off hardware circuit is configured to detect the shutdown action of the on/off key and a shutdown control signal sent by the on/off control module and send a signal to cut off the power supply. The control apparatus can reduce the probability of accidental shutdown caused by system software and hardware failure or man-made misoperation and improve the operating reliability of the robot- (Continued)

assisted surgical device without significantly increasing cost.

18 Claims, 5 Drawing Sheets

(56) References Cited

U.S. PATENT DOCUMENTS

| | | | |
|---|---|---|---|
| 6,598,168 B1 | 7/2003 | Chen | |
| 9,841,805 B2* | 12/2017 | Shimada | G06F 1/324 |
| 2006/0236132 A1 | 10/2006 | Chen et al. | |
| 2007/0083777 A1* | 4/2007 | Morisawa | G06F 9/4401 |
| | | | 713/300 |
| 2007/0106915 A1* | 5/2007 | Shie | G06F 1/24 |
| | | | 713/300 |
| 2007/0220282 A1* | 9/2007 | Huang | G06F 1/26 |
| | | | 713/300 |
| 2011/0239028 A1* | 9/2011 | Higuma | G06F 1/266 |
| | | | 713/340 |
| 2012/0214557 A1* | 8/2012 | Lin | G06F 1/24 |
| | | | 455/572 |
| 2014/0122905 A1* | 5/2014 | Chen | G06F 1/26 |
| | | | 713/300 |
| 2014/0143528 A1* | 5/2014 | Tsutsui | G06F 1/24 |
| | | | 713/1 |
| 2015/0070179 A1* | 3/2015 | Wu | G06F 11/3058 |
| | | | 340/603 |
| 2018/0300239 A1* | 10/2018 | Hsu | G06F 3/0619 |
| 2021/0256241 A1* | 8/2021 | Baker | G06F 1/32 |
| 2022/0058027 A1* | 2/2022 | Wu | G06F 1/28 |

FOREIGN PATENT DOCUMENTS

| | | | |
|---|---|---|---|
| CN | 202435363 U | 9/2012 | |
| CN | 104360716 A | 2/2015 | |
| CN | 104901664 A | 9/2015 | |
| CN | 105100534 A | 11/2015 | |
| CN | 205540123 U | 8/2016 | |
| CN | 106156661 A | 11/2016 | |
| CN | 205847223 U | 12/2016 | |
| CN | 206080684 U | 4/2017 | |
| CN | 206848886 U | 1/2018 | |
| CN | 108418270 A | 8/2018 | |
| CN | 109754874 A | 5/2019 | |
| JP | 58087601 A | 5/1983 | |
| JP | 0221518 A | 1/1990 | |
| JP | 09218702 A | 8/1997 | |
| JP | 2010119271 A | 5/2010 | |

OTHER PUBLICATIONS

Supplementary European Search Report in corresponding European Application No. EP19903448, dated Dec. 2021 (3 pages).
Chinese Office Action in corresponding Chinese Application No. 2018116108705 dated Jun. 19, 2020 (2 pages).
International Search Report in corresponding PCT Application No. PCT/CN2019/129036 dated Mar. 26, 2020 (5 pages).
Office Action in related Canadian Application No. 3118935 dated Jul. 17, 2023 (7 pages).

* cited by examiner

U.S. 11,803,392 B2

ACCIDENTAL-SHUTDOWN-PROOF SWITCH CONTROL APPARATUS AND METHOD FOR ROBOT-ASSISTED SURGICAL DEVICE

CROSS-REFERENCE TO RELATED APPLICATIONS

This patent application is a U.S. National Phase of International Application No. PCT/CN2019/129036, filed on Dec. 27, 2019, which claims priority to Chinese Patent Application No. 201811610870.5, filed on Dec. 27, 2018. The entire contents of each of the above-identified applications are incorporated herein by reference.

TECHNICAL FIELD

The disclosure relates to an accidental-shutdown-proof switch control apparatus and an accidental-shutdown-proof switch control method for robot-assisted surgical devices, and relates to the technical field of medical instruments.

BACKGROUND

Robot-assisted surgery (also referred to as robotic-assisted surgery) is a popular direction in the current surgical field. A surgical device which employs advanced robot technology can greatly improve the surgical operation capability and the surgical efficiency of surgeons, and reduce the working strength and pressure of surgeons. Thus, it is popular. But the robot-assisted surgical device is an electrical device and has a failure risk (it must meet the detection requirement for single failure in the medical instrument industry standard, that is, a failure of a component in the instrument can be detected, and the failure does not result in a harm risk to a user or patient). If during a robot-assisted surgery, a shutdown button is accidentally pressed by mistake or other factors lead to wrong shutdown signal, the robot-assisted surgical device in work is directly shut down, so that the surgery has to be interrupted, the treatment is delayed, and a patient is in dangerous in serious cases.

As shown in FIG. 1, at present, many common medical device employ a hardware shutdown circuit to realize the shutdown function. Once the shutdown button is pressed, the relay in the corresponding shutdown circuit acts immediately, so that the irreversible shutdown procedure is started. This method is obviously not suitable for robot-assisted surgical device, especially device for executing surgical operations.

As shown in FIG. 2, current da Vinci surgical robot (Intuitive surgical, Inc.) which is widely applied in the world adopts a pure software control to realize shutdown, that is, the shutdown button does not directly control the hardware shutdown circuit, but connected to the corresponding control chip that collects a state of the button. When it is detected that the shutdown button is pressed, the software starts the shutdown procedure and displays shutdown information on man-machine interface. If there is no action on the shutdown button within 10 s, then the control module informs other functional modules of the system to shut down. After the corresponding shutdown task is completed, finally, the control module outputs a signal to control the hardware shutdown circuit to cut off system power supply and complete shutdown. If the control chip detects that, within 10 s, the shutdown button is released and pressed again, then the shutdown procedure is interrupted. This method can prevent the shutdown button from being touched by mistake or the button from failing accidentally to cause the system shutdown by mistake. But it cannot prevent the accidental-shutdown caused by the corresponding software failure (additional redundant hardware is needed to realize the error correction)

In summary, in order to prevent the accidental-shutdown action possibly generated in the pure hardware on/off control mode, the robot-assisted surgical device generally adopts a pure software control mode to realize shutdown, so that unexpected accidental-shutdown operation can be prevented. However, the software part for controlling the shutdown procedure cannot be prevented from failing to cause accidental-shutdown. If accidental-shutdown signals caused by the failure of the software part need to be prevented, additional chips need to be added to realize redundant control, so that research and development cost and material cost are greatly increased.

SUMMARY

In view of the above problems, an objective of the present disclosure is to provide an accidental-shutdown-proof control device and an accidental-shutdown-proof control method for robot-assisted surgical device. The accidental-shutdown-proof control device and the accidental-shutdown-proof control method for the robot-assisted surgical device can prevent accidental-shutdown caused by mistouch of a shutdown button or a button failure, and can also prevent accidental-shutdown caused by software failure.

Thus, the present disclosure discloses the following technical solutions:

In a first aspect, the present disclosure provides an accidental-shutdown-proof control device for robot-assisted surgical device, comprising: an on/off key operable to trigger a start action or a shutdown action; an on/off control module operable to detect the shutdown action of the on/off key and obtain a shutdown intention through man-machine interaction; an on/off hardware circuit operable to detect the start action and send a signal to supply power. The on/off hardware circuit is operable to detect the shutdown action of the on/off key and a shutdown control signal sent by the on/off control module and send a signal to cut off power supply.

In some embodiments, the accidental-shutdown-proof control device for the robot-assisted surgical device above further comprises a system power supply module connected with a power supply to supply power to an electrical module of the robot-assisted surgical device. The system power supply module includes a power supply on/off control circuit.

In some embodiments, in the accidental-shutdown-proof control device for the robot-assisted surgical device above, the on/off key comprises a switch button which is responsible for triggering start and shutdown functions, or the on/off key comprises two on/off buttons for starting up and shutting down, respectively.

In some embodiments, in the accidental-shutdown-proof control device for the robot-assisted surgical device above, the on/off hardware circuit comprises an on/off key detection circuit, a start action circuit and a shutdown action circuit. An input terminal of the on/off key detection circuit is connected with the on/off key to detect a state of the on/off key and output a corresponding control signal, a start key-pressing action triggers the on/off key detection circuit to output a start control signal and output the start control signal to the start action circuit, a shutdown key-pressing action triggers the on/off key detection circuit to output hardware shutdown signal and output the hardware shutdown signal to the shutdown action circuit. After receiving the start control signal, the start action circuit controls conduction of a power supply on/off control circuit in the system power supply module to supply power and start up. When the shutdown action circuit receives the hardware shutdown signal and software shutdown signal sent by the on/off control module, the shutdown action circuit controls the power supply on/off control circuit to cut off the power supply and shutdown.

In some embodiments, in the accidental-shutdown-proof control device for the robot-assisted surgical device above, the on/off control module comprises a controller, an input circuit and an output circuit. The input circuit receives a shutdown key signal from the on/off key detection circuit. The controller outputs the software shutdown signal to the shutdown action circuit via the output circuit when the controller obtains shutdown intention of the operator via man-machine interaction.

In some embodiments, in the accidental-shutdown-proof control device for the robot-assisted surgical device above, the system power supply module further comprises an AC/DC voltage conversion module operable to convert an external AC network voltage into a DC voltage required by a module of the system, an output terminal of the AC/DC voltage conversion module is operable to provide voltage required by an operation of the on/off hardware circuit, and the output terminal of the AC/DC voltage conversion module is connected with the power supply on/off control circuit.

In some embodiments, in the accidental-shutdown-proof control device for the robot-assisted surgical device above, the output of the AC/DC conversion module is respectively connected in series with a terminal of a normally open contact of a relay or a terminal of a normally open contact of a delay relay, and another terminal of the AC/DC conversion module is connected with a system function module.

In some embodiments, in the accidental-shutdown-proof control device for the robot-assisted surgical device above, the on/off hardware circuit at least comprises a first relay, a second relay, a third relay, a fourth relay, a fourth relay, a fifth relay, a delay relay, drain diodes and a current-limiting resistor; a control coil of the first relay and the first drain diode are connected in parallel and have a terminal connected to operating voltage and another terminal connected to a terminal of a normally closed contact of the second relay; another terminal of the normally closed contact of the second relay is connected with a terminal of a normally open contact of the first relay and a normally closed contact of the third relay connected in parallel, another terminal of the normally open contact of the first relay and another terminal of the normally closed contact of the third relay are connected in parallel and connected to a terminal of the on/off key, and another terminal of the on/off key is connected to a reference ground; a control coil of the third relay, a second drain diode, a control coil of the delay relay and a third drain diode are connected in parallel and have a terminal connected to the operating voltage and another terminal connected to a terminal of the normally closed contact of the second relay, another terminal of the normally closed contact of the second relay is connected with a terminal of the normally open contact of the first relay and the normally open contact of the third relay connected in parallel, and another terminal of the normally open contact of the first relay and the normally open contact of the third relay is connected to a reference ground; a control coil of the second relay and a fourth drain diode are connected in parallel and have a terminal connected to the operating voltage and another terminal connected to a terminal of a normally open contact of the fourth relay, another terminal of the normally open contact of the fourth relay is connected with a normally closed contact of the first relay, another terminal of the normally closed contact of the first relay is connected with a terminal of a normally open contact of the second relay and a normally open contact of the third relay connected in parallel, another terminal of the normally open contact of the second relay and the normally open contact of the third relay connected in parallel is connected in parallel with a terminal of the on/off key, and another terminal of the on/off key is connected to a reference ground; a control coil of the fifth relay and a fifth drain diode are connected in parallel and have a terminal connected to the operating voltage and another terminal connected to a terminal of the on/off key, and another terminal of the on/off key is connected to a reference ground; the current limiting resistor has a terminal connected to the operating voltage and another terminal connected to the normally open contact of the third relay, another terminal of the normally open contact is connected to an anode of an indicator in the on/off key, and a cathode of the indicator is connected to the reference ground.

In some embodiments, in the accidental-shutdown-proof control device for the robot-assisted surgical device above, the on/off control module comprises a control chip, a control coil of the fourth relay and a drain diode are connected in parallel and have a terminal connected with an output terminal of the control chip and another terminal connected with reference ground, a terminal of a normally open contact of the fourth relay is connected to an operating voltage, another terminal of the normally open contact of the fourth relay is connected with an input terminal of the control chip, a terminal of a normally open contact of the fifth relay is connected with the operating voltage, another terminal of the normally open contact of the fifth relay is connected with the input terminal of the control chip, and the control chip is connected with the man-machine interaction module via a communication interface to realize communication.

In a second aspect, the present disclosure provides a method for controlling the accidental-shutdown-proof control device for the robot-assisted surgical device, comprising the following steps:

step S1, preparing for starting:

before the robot-assisted surgical device starts, the system power supply module is connected with an external network voltage to supply power to the on/off hardware circuit;

step S2, starting:

triggering, by the on/off key, the start action to provide corresponding operating voltage to a module of the system and complete the start action;

step S3, shutdown and prevent accidental-shutdown:

after the start action is completed, the system enters power-on state and the module is electrified to start work, detecting, by the on/off control module, the shutdown action of the on/off key, and obtaining shutdown intention through man-machine interaction, if the on/off key is pressed again;

if the on/off hardware circuit detects the shutdown action of the on/off key and the shutdown control signal sent by the on/off control module, controlling the system power supply module to cut off the power supply and make the system enter an off state;

if the on/off hardware circuit does not detect both the shutdown action of the on/off key and the shutdown control signal sent by the on/off control module, determining a wrong shutdown operation.

Present disclosure discloses above technical solutions which can bring following advantages: compared with other robot-assisted surgical systems adopting a software shutdown mode, the on/off control device of the robot-assisted operation control system provided by the disclosure includes an on/off hardware circuit for detecting the start action to control the system power supply module to supply power. The on/off hardware circuit controls the system power supply module to cut off the power supply when the on/off hardware circuit detects both the shutdown action and the shutdown control signal sent by the on/off control module. Therefore, under little increase of the cost, the probability of accidental shutdown possibly caused by system software and hardware failure or man-made mis-operation can be reduced, and the operating reliability of device is further improved.

DETAILED DESCRIPTION

In order to make objectives, technical solutions, and advantages of embodiments of the present disclosure clear, the technical solutions in the embodiments of the present disclosure will be described clearly and completely with reference to accompanying drawings in the embodiments of the present disclosure. Obviously, a part of, rather than all of, the embodiments of the present disclosure are described. Based on the embodiments of the present disclosure, all other embodiments obtained by one of ordinary skill in the art without inventive work shall fall within the protection scope of the present disclosure.

Figure 1:
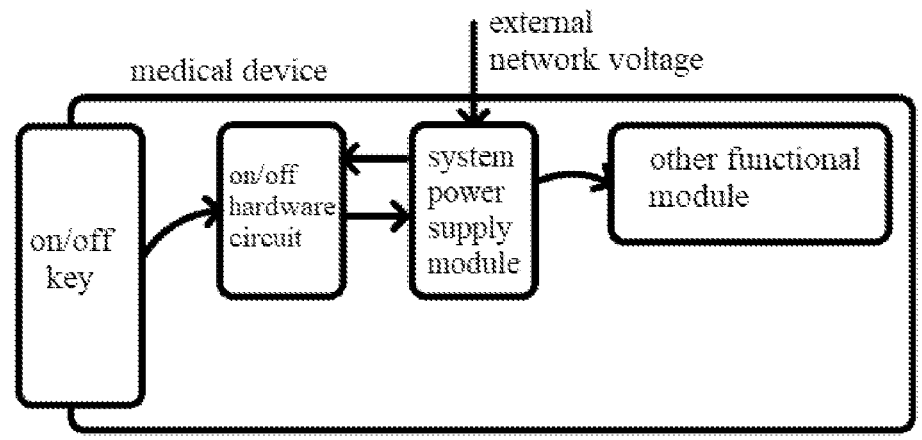
FIG. 1 illustrates a conventional medical device using a pure hardware on/off circuit control system to power-on/power-off.
Figure 2:
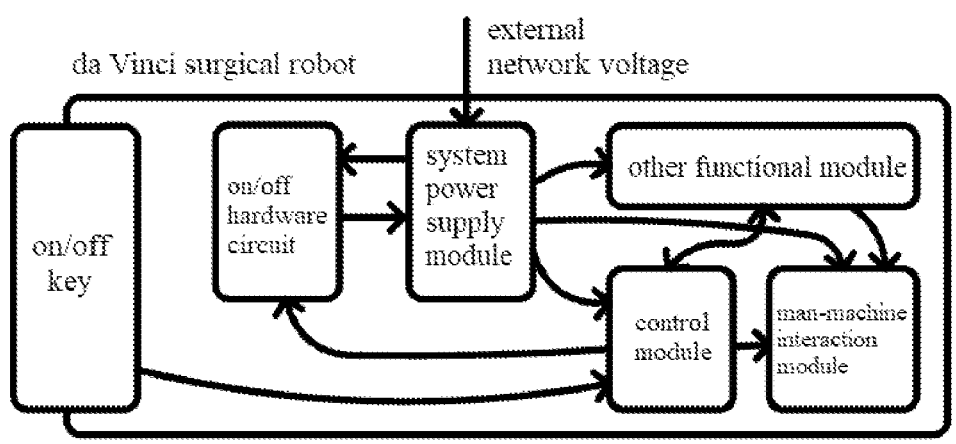
FIG. 2 is a da Vinci surgical robotic system using a software to control an on/off circuit to control power on/off of the system.
Figure 3:
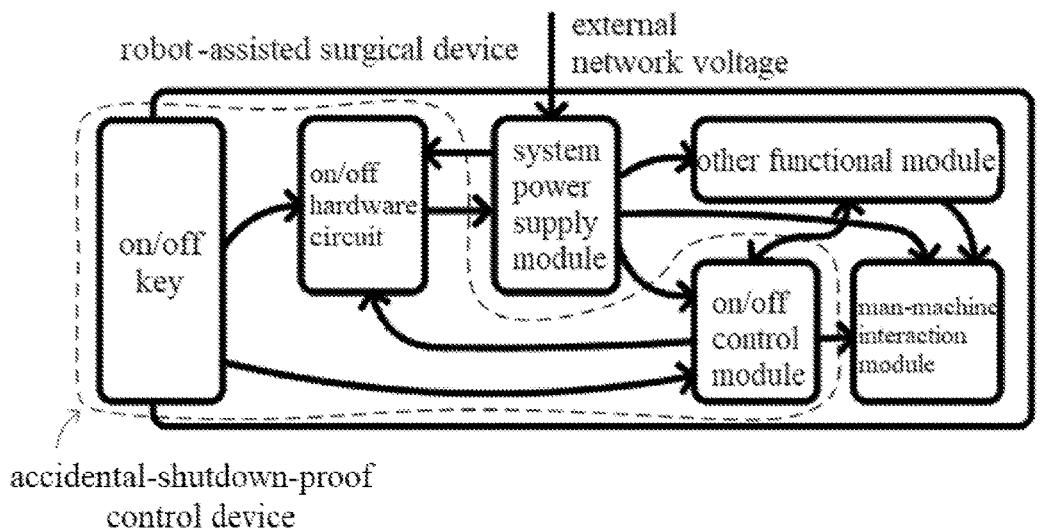
FIG. 3 is a logic block diagram of an on/off control of a robot-assisted surgical device employing an on/off control device of the present disclosure.

As shown in FIG. 3, the disclosure provides an accidental-shutdown-proof control device for robot-assisted surgical device. The accidental-shutdown-proof control device includes an on/off key, an on/off hardware circuit, a system power supply module, an on/off control module and a man-machine interaction module.

The on/off key is used to control the on/off action of the on/off hardware circuit. It is appreciated that the on/off key can directly trigger start or shutdown action of the on/off hardware circuit, but cannot directly trigger and control the off action of the on/off hardware circuit.

The system power supply module is connected with an external power supply to provide required operating voltage for each power consuming module of the robot-assisted surgical device.

The on/off hardware circuit can control the system power supply module to supply power or cut off power supply.

The on/off control module can detect a state of the on/off key, output a shutdown control signal and provide information prompt to an operator through the man-machine interaction module. when the on/off key is pressed, the on/off control module can detect the corresponding button signal and provide information prompt to the operator through the man-machine interaction module. A shutdown control signal of the on/off control module is output to the on/off hardware circuit. When both shutdown control signal and the on/off key hardware signal exist, a shutdown action of the on/off hardware circuit can be triggered.

Figure 4:
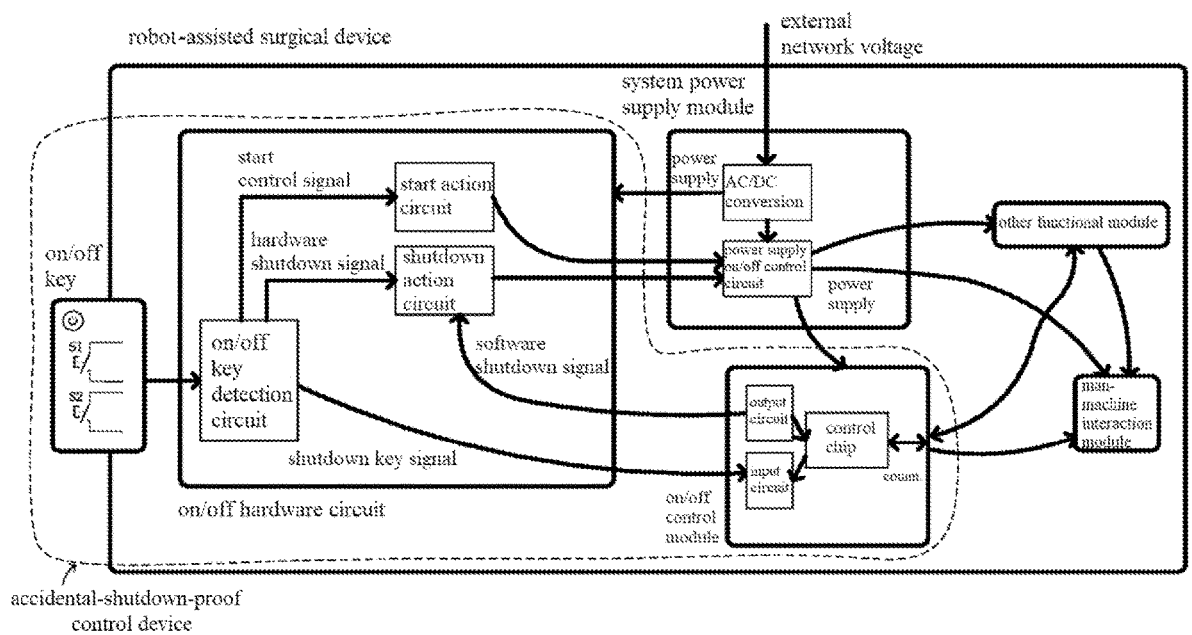
FIG. 4 is a schematic illustration of the on or off operation of a robot-assisted surgical device employing an on/off control device of the present disclosure.

In an exemplary embodiment, as shown in FIG. 4, the on/off key may include a switch button that is responsible for triggering start and shutdown function. Alternatively, the on/off key may include two switch buttons, one switch button for triggering the start action and another switch button for triggering the shutdown action. The present disclosure is not limited here and can use a setting according to actual requirement.

In an exemplary embodiment, the on/off hardware circuit includes an on/off key detection circuit, a start action circuit and a shutdown action circuit. An input terminal of the on/off key detection circuit is connected with the on/off key to detect a state of the on/off key and output a corresponding control signal. A start key-pressing action can trigger the on/off key detection circuit to output a start control signal, and output the start control signal to the start action circuit. After receiving the start control signal, the start action circuit controls the conduction of a power supply on/off control circuit in system power supply module to supply power to each functional module of the system, so as to start up. A shutdown key-pressing action can trigger correspondent hardware shutdown signal. The hardware shutdown signal is transmitted to the shutdown action circuit. The signal does not immediately trigger the shutdown action circuit to control the power supply on/off control circuit in the system power supply module to cut off the power supply. When the shutdown action circuit also receives the shutdown control signal sent by the on/off control module, the power supply on/off control circuit in the system power supply module is triggered and controlled to cut off the power supply and shutdown the device. In addition, when an off key is pressed, the on/off key detection circuit can be triggered to transmit a corresponding level signal to the on/off control module, so that the on/off control module can determine shutdown intention of a user through the man-machine interaction module.

In an exemplary embodiment, the on/off control module includes a controller, an input circuit and an output circuit. The input circuit receives a shutdown key signal from the on/off key detection circuit, and inputs it to the controller. The controller outputs the shutdown control signal to a shutdown action circuit through the output circuit, which cooperates with the hardware shutdown control signal to realize shutdown. In addition, the controller can also communicate with other functional modules of the system and the man-machine interaction module through the communication interface.

In an exemplary embodiment, the system power supply module includes an AC/DC voltage conversion module and a power supply on/off control circuit. The AC/DC voltage conversion module can convert the voltage of an external alternating current network into direct current voltage required by each module of the system. The AC/DC voltage conversion module directly provides the voltage required by the on/off hardware circuit. The AC/DC voltage conversion module also outputs the voltage to the power supply on/off control circuit and is controlled by the on/off hardware circuit to supply power to other modules of the system.

The specific implementation of the accidental-shutdown-proof control device for robot-assisted surgical device of the present disclosure is described in detail by way of specific examples below.

Figure 5:
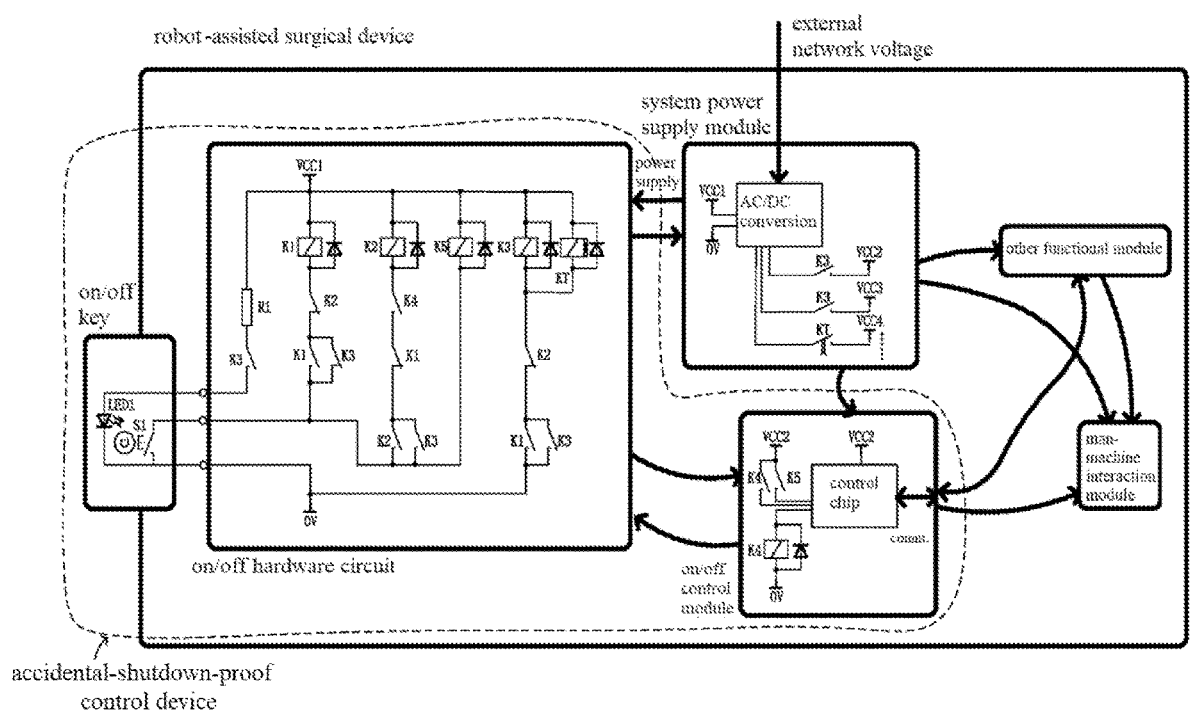
FIG. 5 is an implementation of an accidental-shutdown-proof control device according to the present disclosure.
Figure 6:
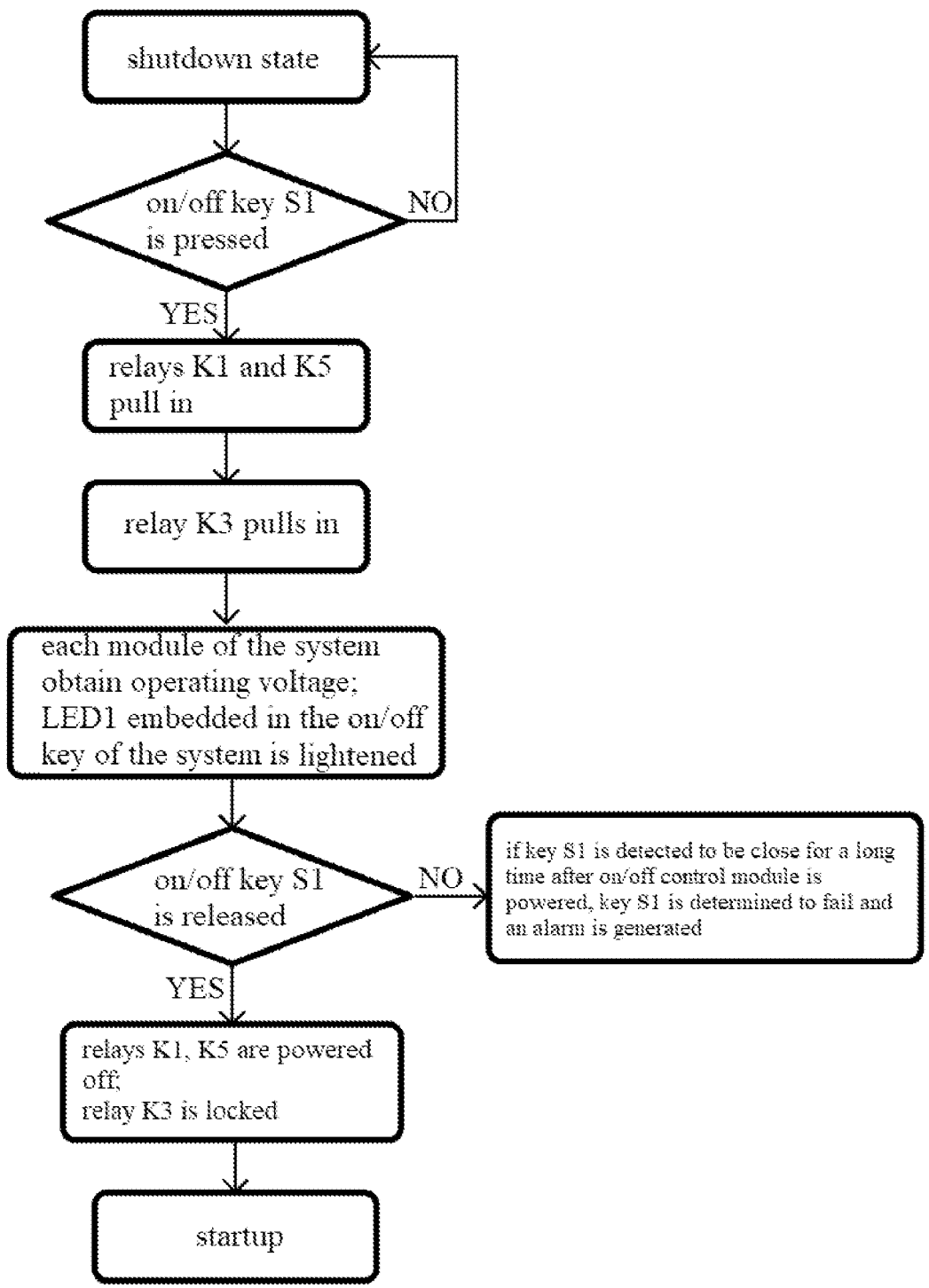
FIG. 6 is a start control flow diagram of an accidental-shutdown-proof control device according to the present disclosure.
Figure 7:
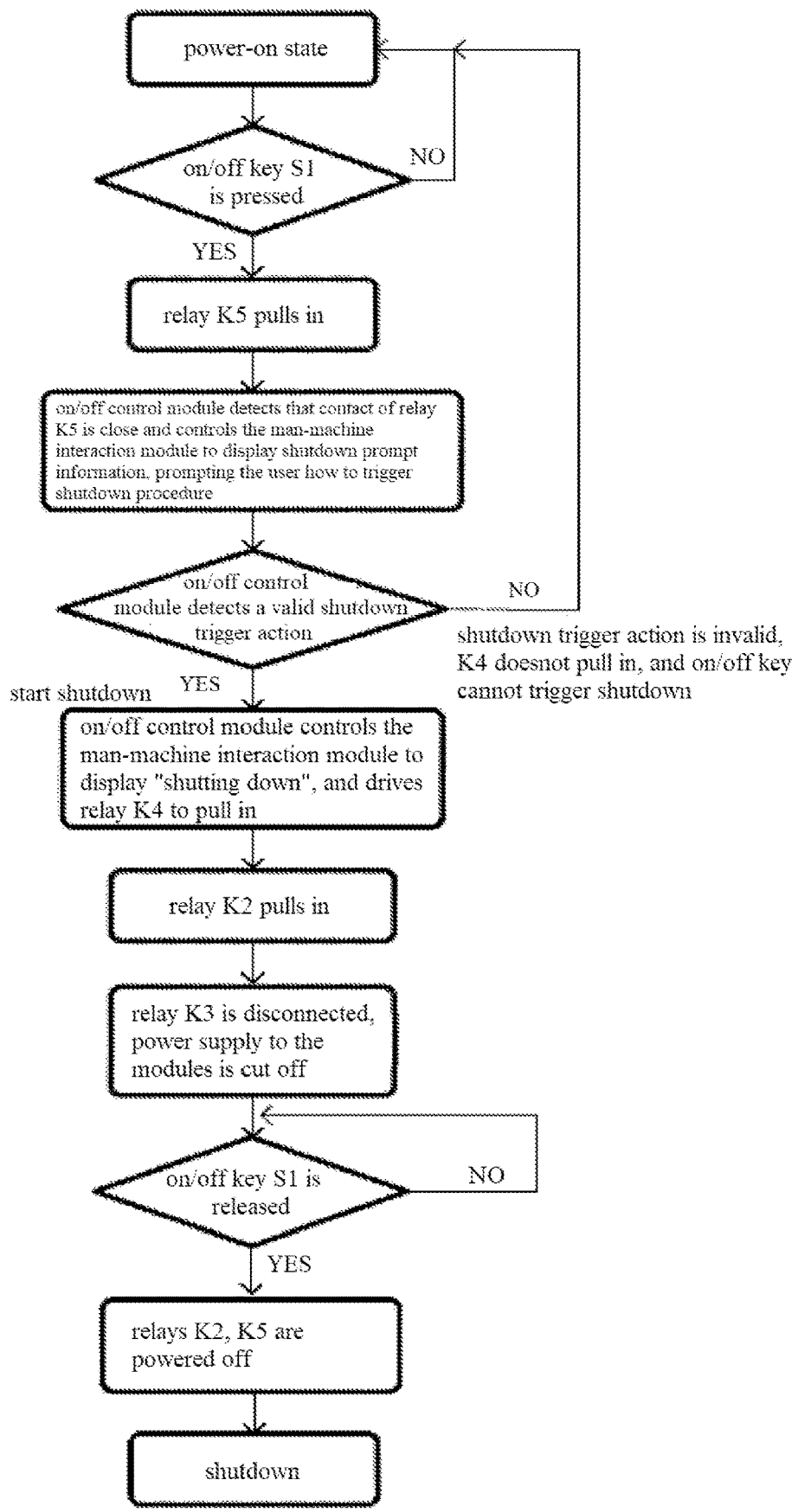
FIG. 7 is a shutdown control flow diagram of an accidental-shutdown-proof control device according to the present disclosure

As shown in FIGS. 5-7, the on/off key of the embodiment includes an on/off key S1 and a signal indicator LED1.

In some embodiments, the on/off hardware circuit includes four common relays K1, K2, K3 and K4 and a delay relay KT. In addition, the on/off hardware circuit also includes drain diodes connected with respective relays in parallel and a current limiting resistor R1. A control coil of the relay K1 is connected in parallel with a drain diode. Its one terminal is connected to operating voltage VCC1, and another terminal is connected with a normally closed contact of K2, another terminal of the normally closed contact of K2 is connected with a normally open contact of K1 and a normally closed contact of K3. The normally open contact of the K1 is connected in parallel with the normally closed contact of the K3. Another terminal of the normally open contact of the K1 is connected to a terminal of the on/off key S1, and another terminal of the on/off key S1 is connected to a reference ground. With the circuit loop, a start signal (in an off state, the S1 is pressed) can be detected, and the start action can be realized (the relay K1 pulls in, so that the K3 and the KT pull in, and the power supply can be provided).

The control coil of the relay K3, the control coil of the relay KT and the corresponding drain diodes are connected in parallel. One terminal is connected to the operating voltage VCC1, and another terminal is connected with a normally closed contact of the relay K2. Another terminal of the normally closed contact of the relay K2 is connected with a normally open contact of the relay K1 and a normally open contact of the relay K3. The normally open contact of the relay K1 is connected in parallel with the normally open contact of the relay K3, and another terminal is connected to a reference ground.

The control coil of the relay K2 is connected in parallel with a drain diode. Its one terminal is connected to operating voltage VCC1, and another terminal is connected with a normally open contact of the relay K4. Another terminal of the normally open contact of the relay K4 is connected with a normally closed contact of the relay K1, and another terminal of the normally closed contact of the relay K1 is connected with the normally open contacts of the relay K2 and the relay K3. The normally open contacts of the relay K2 and the relay K3 are connected in parallel, and their other terminals are connected to a terminal of the on/off key S1. Another terminal of the on/off key S1 is connected to the reference ground. With the circuit loop, the shutdown action can be realized (relay K2 pulls in, relay K3 and delay relay KT are opened, realizing shutdown, and thus, only pressing S1 is unable to directly shutdown).

The control coil of the relay K5 is connected in parallel with a drain diode. Its one terminal is connected to operating voltage VCC1, and another terminal is connected to a terminal of the on/off key S1. Another terminal of the on/off key S1 is connected to the reference ground. With the circuit loop, whether the on/off key S1 is pressed can be detected (if the on/off key S1 is pressed, the relay K5 pulls in), which can be fed back to the control chip in the on/off control module for determining the shutdown intention of a user.

A terminal of the resistor R1 is connected to the operating voltage VCC1, and another terminal of the resistor R1 is connected with a normally open contact of the relay K3. Another terminal of the normally open contact is connected to an anode of the indicator LED1 in the on/off key, and a cathode of the indicator LED1 is connected to the reference ground. When the relay K3 pulls in, the normally open contact of the relay K3 is closed, so that the indicator LED1 emits light and can indicate the on state.

In some embodiments, the system power supply module includes one or more AC/DC conversion modules. The output VCC1 of the AC/DC conversion module directly provides operating voltage for an on/off hardware circuit, and other voltage outputs are firstly connected in series with a normally open contact of a relay K3 or a normally open contact of a delay relay KT and then connected to system functional modules for supplying power to the system functional modules.

In some embodiments, the on/off control module includes a control chip. A control coil of relay K4 is connected in parallel with a drain diode. Its one terminal is connected with output of control chip, and another terminal is connected to the reference ground. Relay K4 is driven by the control chip to output software shutdown signal. A terminal of a normally open contact of a relay K4 is connected to an operating voltage VCC2, and another terminal is connected to an input of the control chip. The control chip can detect whether relay K4 fails to open. A terminal of a normally open contact of the relay K5 is connected to the operating voltage VCC2, and another terminal is connected to the control chip. The control chip can detect whether the on/off key is pressed. The control chip can communicate with the man-machine interaction module and other functional modules of the system through communication interface.

Based on the embodiments above, the operating process of the accidental-shutdown-proof control device for the robot-assisted surgical device includes the following.

1. Start Preparation Process:

The on and off of the robot-assisted surgical device is triggered by the same key S1. Before the robot-assisted surgical device is started, the system power supply module is connected with an external network voltage and begins to supply power VCC1 to the on/off hardware circuit. The power supplies (VCC2, VCC3 and the like) of other modules of the system are disconnected because the relay K3 of the system power supply module does not pull in.

2. Start Process:

The on/off key S1 is pressed. The relay K1 pulls in, and all contacts of the relay K1 act, so that the relay K3 is electrified to pull in. The normally open contact of the relay K3 is closed, so that each module of the system can obtain corresponding operating voltage. The system is started. An indicator LED1 embedded in the on/off key of the system is lightened because the normally open contact of the relay K3 is closed. Relay K2 cannot pull in due to disconnection of the normally open contact of the relay K4 and the normally closed contact of the relay K1. The relay K5 is electrified to pull in, and thus its contact feedbacks that on/off key S1 is pressed. When the on/off key S1 is released, the coil of the relay K1 is powered off, and because the normally open contact of the relay K3 is closed, the coil of the relay K3 is not powered off due to disconnection of the normally closed contact of the relay K1. The relay K5 is powered off due to the disconnection of the on/off key S1 to feed back that the key is released.

3. Shutdown Process and Prevent Accidental-Shutdown:

After the start action is completed, the system enters a power-on state, and the modules are powered on and start to work. If the on/off key S1 is pressed again (whether intentionally or unintentionally, or the on/off key S1 is closed due to hardware failure), only the relay K5 is electrified and pull in. The relay K1 cannot be electrified due to the fact that the normally closed contact of the relay K3 is disconnected. The relay K2 cannot be electrified due to the fact that the normally open contact of the relay K4 is not closed. Thus, the system can still continue to work normally.

The on/off control module detects that the on/off key is pressed (the normally open contact of the relay K5 is changed from open to close, and the control chip can detect the change of the corresponding level signal). After detecting that the on/off key is pressed, the on/off control module controls the man-machine interaction module to display shutdown prompt information through the communication interface, prompting the user how to operate to trigger the shutdown procedure, such as "the shutdown button has been pressed, if you want to confirm shutdown, please release the button after 5 s, then press the shutdown button again and remain pressed for more than 3 s" (the action combination for triggering shutdown is not limited in this respect, and other action combinations can be used). The on/off control module (through reading the state of the normally open contact of the relay K5) continuously collects the state of the on/off key, to determine whether a predetermined shutdown trigger action is implemented. If the corresponding shutdown trigger action is not implemented (for example, the shutdown button is released within 5 s after the first pressing, or it is not pressed again after release, or alternatively, it may be held for less than 3 s after being pressed again), the on/off control module determines that the shutdown trigger action is invalid, and continuously waits for the next shutdown trigger action. If the shutdown trigger action is realized, then the on/off control module determines that the shutdown triggering is successful. The on/off control module controls the man-machine interaction module to display the information of "shutting down", and the on/off control module drives the relay K4 to pull in. Once the on/off key is pressed, the relay K2 is electrified to pull in, so that the relay K3 is disconnected. The power supply of the system power supply module to the modules of the system is cut off (the power supply VCC1 of the on/off hardware circuit is not affected, so that the power supply required by the start or shutdown action is still on). The on/off key LED1 is extinguished, and the system enters a shutdown state.

Moreover, if some important functional modules exist in the system and need time to complete some important tasks before shutdown (for example, some important data need to be saved before shutdown), a delay relay KT can be used to control the corresponding power-off to ensure that enough time is left to complete the important tasks after the shutdown action. In addition, an uninterruptible power supply (UPS) can also be used for supplying power to an important functional module. The UPS is turned off after the important functional module completes tasks, so that time-delay power off is realized, and the completion of the important tasks is not interrupted by shutdown.

Based on the disclosure and teaching of the foregoing description, those skilled in the related art can also make appropriate changes and modifications to the foregoing embodiments. Therefore, the present disclosure is not limited to the specific embodiments disclosed and described above, and some modifications and changes to the present disclosure should also fall within the protection scope of the claims of the present disclosure. In addition, although some specific terms are used in this disclosure, these terms are only for convenience of description and do not constitute any limitation to the present disclosure.

The invention claimed is:

1. An on/off control device, comprising:
an on/off key configured to trigger a start action or a shutdown action;
an on/off control module configured to detect the shutdown action of the on/off key and obtain a shutdown intention through roan-machine interaction; and
air on/off hardware circuit configured to send a signal for cutting off power supply based on a hardware shutdown signal triggered by the on/off key and a shutdown control signal sent by the on/off control module,
wherein:
the on/off hardware circuit comprises a first relay, a second relay, a third relay, and a fourth relay;
a control coil of the first relay, a closed contact of the second relay, a parallel connection of an open contact of the first relay, and a closed contact of the third relay are connected in series with the on/off key;
a control coil of the second relay, a closed contact of the first relay, an open contact of the fourth relay, a parallel connection of an open contact of the second relay, and an open contact of the third relay are connected in series with the on/off key; and
a control coil of the third relay, the closed contact of the second relay, the parallel connection of the open contact of the first relay, and the open contact of the third relay are connected in series.

2. The on/off control device of claim 1, wherein:
the on/off key comprises a switch button for toggling between start and shutdown functions; or
the on/off key comprises an on button for starting up and an off button for shutting down.

3. The on/off control device of claim 1, further comprising a system power supply module comprising a power supply on/off control circuit.

4. The on/off control device of claim 3, wherein:
the on/off hardware circuit comprises an on/off key detection circuit and a shutdown action circuit;
an input terminal of the on/off key detection circuit is connected with the on/off key to detect a state of the on/off key and output a corresponding control signal;
the on/off key detection circuit is configured to output, based on a shutdown key-pressing action, the hardware shutdown signal to the shutdown action circuit; and
the shutdown action circuit is configured to control, based on the hardware shutdown signal and the shutdown control signal sent by the on/off control module, the power supply on/off control circuit to cut off the power supply.

5. The on/off control device of claim 4, wherein:
the on/off hardware circuit further comprises a start action circuit;
the on/off key detection circuit is configured to output, based on a start key-pressing action, a start control signal to the start action circuit; and
the start action circuit is configured to control, based on the start control signal, the power supply on/off control circuit to supply power.

6. The on/off control device of claim 4, wherein:
the on/off control module comprises a controller, an input circuit, and an output circuit;
the input circuit is configured to receive a shutdown key signal from on/off key detection circuit; and
the controller is configured to output the shutdown control signal to the shutdown action circuit via the output circuit based on shutdown intention obtained via the man-machine interaction.

7. The on/off control device of claim 3, wherein the system power supply module further comprises an AC/DC voltage conversion module configured to convert an external AC network voltage into a DC voltage,
wherein:
an output terminal of the AC/DC voltage conversion module is configured to provide voltage to the on/off hardware circuit; and
the output terminal of the AC/DC voltage conversion module is connected with the power supply on/off control circuit.

8. The on/off control device of claim 7, wherein:
an output of the AC/DC voltage conversion module is connected in series with a terminal of an open contact of a relay or a terminal of an open contact of a delay relay; and
another terminal of the AC/DC voltage conversion module is connected with a system function module.

9. The on/off control device of claim 1, wherein the on/off hardware circuit further comprises a delay relay, wherein a control coil of the delay relay is connected in parallel with the control coil of the third relay.

10. The on/off control device of claim 9, wherein the on/off hardware circuit further comprises at least one drain diode connected in parallel with a control coil of at least one of the first relay, the second relay, the third relay, the fourth relay, a fifth relay, or the delay relay.

11. The on/off control device of claim 1, wherein the on/off hardware circuit further comprises a current-limiting resistor and an indicator, wherein the current-limiting resistor, the indicator, and the open contact of the third relay are connected in series with the on/off key.

12. The on/off control device of claim 1, wherein the on/off hardware circuit further comprises a fifth relay, wherein a control coil of the fifth relay is connected in series with the on/off key.

13. The on/off control device of claim 12, wherein:
the on/off control module comprises a control chip;
a control coil of the fourth relay and a drain diode are connected in parallel and have a terminal connected with an output terminal of the control chip and another terminal connected with reference ground;
a terminal of an open contact of the fourth relay is connected to an operating voltage;
another terminal of the open contact of the fourth relay is connected with an input terminal of the control chip;
a terminal of an open contact of the fifth relay is connected with the operating voltage;
another terminal of the open contact of the fifth relay is connected with the input terminal of the control chip; and
the control chip is connected with a man-machine interaction module via a communication interface to facilitate communication.

14. A method for controlling an on/off control device, the on/off control device comprising an on/off key configured to trigger a start action or a shutdown action, an on/off control module configured to detect the shutdown action of the on/off key and obtain a shutdown intention through man-machine interaction, and an on/off hardware circuit configured to send a signal for cutting off power supply based on a hardware shutdown signal triggered by the on/off key and a shutdown control signal sent by the on/off control module, the method comprising:

detecting, by the on/off hardware circuit, the shutdown action of the on/off key;
obtaining, by the on/off control module, the shutdown action of the on/off key;
obtaining, by the on/off control module, shutdown intention through man-machine interaction; and
sending, by the on/off hardware circuit, based on the hardware shutdown signal triggered by the shutdown action and the shutdown control signal sent by the on/off control module, the signal for cutting off the power supply,
wherein:
the on/off hardware circuit comprises a first relay, a second relay, a third relay, and a fourth relay;
a control coil of the first relay, a closed contact of the second relay, a parallel connection of an open contact of the first relay and a closed contact of the third relay are connected in series with the on/off key;
a control coil of the second relay, a closed contact of the first relay, an open contact of the fourth relay, a parallel connection of an open contact of the second relay and an open contact of the third relay are connected in series with the on/off key; and
a control coil of the third relay, the closed contact of the second relay, the parallel connection of the open contact of the first relay, and the open contact of the third relay are connected in series.

15. A robot-assisted surgical device, comprising:
at least one functional module;
a man-machine interaction module configured to receive a shutdown intention from an operator; and
an on/off control device configured to control power supply of the at least one functional module, the on/off control device comprising:
an on/off key configured to trigger a start action or a shutdown action;
an on/off control module configured to detect the shutdown action of the on/off key and obtain the shutdown intention through the man-machine interaction module; and
an on/off hardware circuit configured to send a signal for cutting off power supply based on a hardware shutdown signal triggered by the on/off key and a shutdown control signal sent by the on/off control module,
wherein:
the on/off hardware circuit comprises a first relay, a second relay, a third relay, and a fourth relay;
a control coil of the first relay, a closed contact of the second relay, and a parallel connection of an open contact of the first relay and a closed contact of the third relay are connected in series with the on/off key;
a control coil of the second relay, a closed contact of the first relay, an open contact of the fourth relay, and a parallel connection of an open contact of the second relay, and an open contact of the third relay are connected in series with the on/off key; and
a control coil of the third relay, the closed contact of the second relay, and the parallel connection of the open contact of the first relay, and the open contact of the third relay are connected in series.

16. The robotic-assisted surgical device of claim 15, wherein:
the on/off hardware circuit comprises an on/off key detection circuit and a shutdown action circuit;

an input terminal of the on/off key detection circuit is connected with the on/off key to detect a state of the on/off key and output a corresponding control signal;

the on/off key detection circuit is configured to output, based on a shutdown key-pressing action, the hardware shutdown signal to the shutdown action circuit; and the shutdown action circuit is configured to control, based on the hardware shutdown signal and the shutdown control signal sent by the on/off control module, the power supply on/off control circuit to cut off the power supply.

17. The robot-assisted surgical device of claim 15, wherein the on/off hardware circuit further comprises a fifth relay, wherein a control coil of the fifth relay is connected in series with the on/off key.

18. The robotic-assisted surgical device of claim 15, wherein the on/off hardware circuit further comprises a delay relay, wherein a control coil of the delay relay is connected in parallel with the control coil of the third relay.

* * * * *